United States Patent [19]

Bremer

[11] Patent Number: 4,539,979

[45] Date of Patent: Sep. 10, 1985

[54] TEMPORARY CERVICAL TRACTION MAINTENANCE

[75] Inventor: Paul W. Bremer, Jacksonville, Fla.

[73] Assignee: Bremer Orthopedics, Inc., Jacksonville, Fla.

[21] Appl. No.: 489,076

[22] Filed: Apr. 27, 1983

[51] Int. Cl.³ ............................................. A61H 1/02
[52] U.S. Cl. ........................................ 128/75; 128/78; 128/84 R; 128/69
[58] Field of Search ............... 128/75, 78, 80 R, 87 B, 128/DIG. 23, 84 R, 68, 69; 269/217

[56] References Cited

U.S. PATENT DOCUMENTS

| | | |
|---|---|---|
| 239,356 | 3/1881 | Warren .............................. 269/217 |
| 2,166,229 | 7/1939 | Anderson ................... 128/DIG. 23 |
| 2,706,982 | 4/1955 | Hale et al. . |
| 2,736,314 | 4/1953 | Hale ................................ 128/87 B |
| 3,003,498 | 10/1961 | Hotas .................................... 128/75 |
| 3,336,922 | 8/1967 | Taylor . |
| 3,359,976 | 12/1967 | Laval, Jr. . |
| 3,421,500 | 1/1969 | Jacobson . |
| 3,605,736 | 9/1971 | D'Amico et al. . |
| 3,662,750 | 5/1972 | Jorgensen ........................... 128/75 |
| 3,795,243 | 3/1974 | Miller .................................. 128/75 |
| 3,827,429 | 8/1974 | Heikes ................................ 128/75 |
| 3,915,161 | 10/1975 | Shields ................................ 128/75 |
| 3,957,040 | 5/1976 | Calabrese ........................... 128/75 |
| 4,015,597 | 4/1977 | Beaver ................................ 128/75 |
| 4,194,501 | 3/1980 | Watt .................................... 128/75 |
| 4,250,874 | 2/1981 | Rude .................................... 128/75 |

Primary Examiner—Richard J. Apley
Assistant Examiner—Alan Cannon
Attorney, Agent, or Firm—Cushman, Darby & Cushman

[57] ABSTRACT

A portable cervical traction device is utilized to temporarily positively maintain cervical traction while a patient is transported from a stationary traction station to another station, such as an X-ray station. While the patient is in traction at a traction station, the backplate and shoulder supports of the portable device are attached to the patient. Upstanding from the backplate are a pair of telescoping components with compression springs, and at the top of those components is a cross bar. Slide rods extend outwardly from the cross bar to overhang the shoulder supports, and a slide bar slides along the slide rods. A cam cleat on the slide bar is moved into engagement with the traction cable at the traction site, and suitable counter-traction force is applied by compressing the springs associated with the telescoping components. Then the traction cable is released from its attachment at the traction station, and is wrapped around a deck cleat. The device is utilizable with a cervical strap, tongs, halo, and like traction-facilitating devices.

20 Claims, 4 Drawing Figures

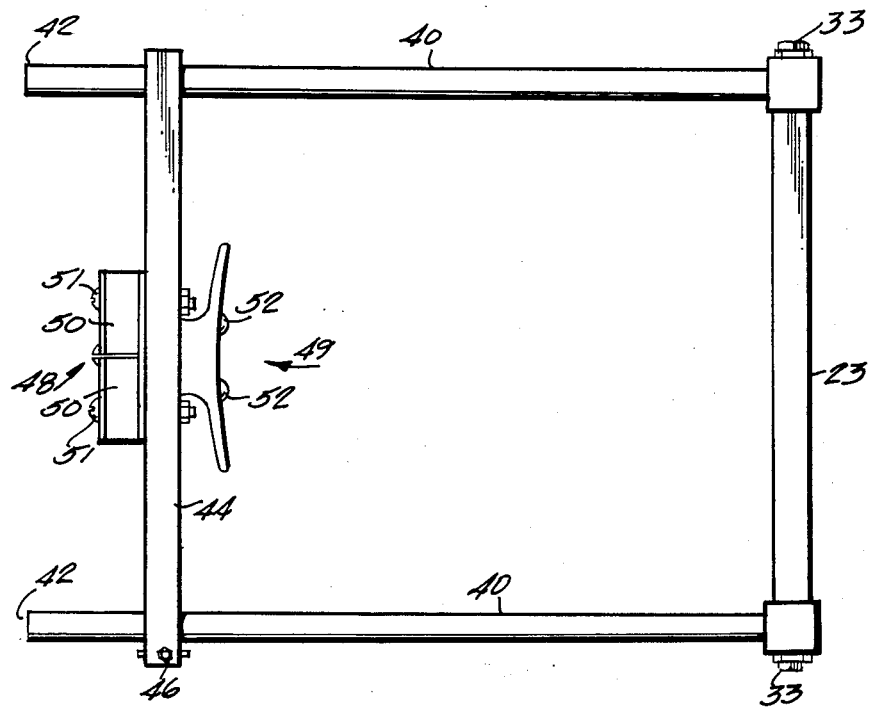

TEMPORARY CERVICAL TRACTION MAINTENANCE

BACKGROUND AND SUMMARY OF THE INVENTION

There are many situations when it is necessary to temporarily move a patient from a bed in which he/she is in regular cervical traction (a traction cable being utilized) to another station, such as an operating room or an area for applying diagnostic or therapeutic radiation (e.g. X-rays) to the patient. When the patient is being transported it is highly desirable to maintain the patient in cervical traction, and according to the present invention it is possible to do this in a simple and readily utilizable manner. The device according to the invention is utilizable with most conventional traction-facilitating devices, such as a cervical strap, tongs, or halo.

The device according to the invention includes shoulder supports which engage the patient's shoulders, and which are preferably attached to a radiolucent backplate. Chest straps are also attached to the backplate and cross over the patient's chest to hold the shoulder supports and backplate in contact with the patient's body.

Attached to the backplate is a lower cross bar, and two sets of telescoping components extend upwardly from the lower cross bar and are joined at the top by an upper cross bar. Each set of telescoping components consists of a tube and a rod with a compression spring disposed in the tube and engaged by the rod. Scale markings are preferably applied to the rod to gauge the amount of force applied by the springs within the tubes.

Attached to the upper cross bar are a pair of slide rods which extend generally perpendicular to the plane defined by the upper and lower cross bars and the telescoping components, and so that they generally overhang the shoulder supports. The slide rods have free ends distal from the upper cross bar.

A slide bar slides along the slide rods and has a traction cable grasping structure associated therewith. The traction cable grasping structure preferably comprises a cam cleat which can quickly and easily engage the cable and hold it in the desired relative position. A deck cleat is preferably mounted to the opposite side of the slide bar from the cam cleat so that after the traction cable is released the cable may be wrapped around the deck cleat.

The portable traction device according to the invention may be easily and quickly applied to the patient. The patient when in bed at the regular traction station is log-rolled onto his/her side, and the backplate of the portable traction device is applied in appropriate position on the patient's back and shoulder. The patient is then log-rolled onto the portable traction device, and the shoulder supports are moved into proper position on the patient's shoulders, and the backplate and the shoulder supports are strapped in place on the patient's body. In this position, the traction cable extends between the free distal ends of the slide rods. The slide bar is then slid on the slide rods until the cam cleat comes in contact with the traction cable. Then the necessary traction force is applied by pushing down on the upper cross bar to compress the springs in the tubes, until the desired force is achieved as determined by reading the scale markings on the telescoping components. The cam cleat holds the cable in position maintaining this traction force, and the traction cable can then be detached from its connection at the traction station. The cable is then wrapped about the deck cleat, and thus cervical traction is positively maintained on the patient while he/she can then be readily transported to another station.

It is the primary object of the present invention to provide a simple yet effective device and method for temporarily maintaining cervical traction on a patient while the patient is transported from a permanent traction station to another station. This and other objects of the invention will become clear from an inspection of the detailed description of the invention, and from the appended claims.

BRIEF DESCRIPTION OF THE DRAWINGS

FIG. 2 is a bottom plan view of the device of FIG. 1;

FIG. 3 is a side elevational view of the device of FIG. 1; and

In FIGS. 2 through 4 the shoulder supports, backplate, and chest straps have been removed for clarity of illustration.

DETAILED DESCRIPTION OF THE DRAWINGS

Figure 1:
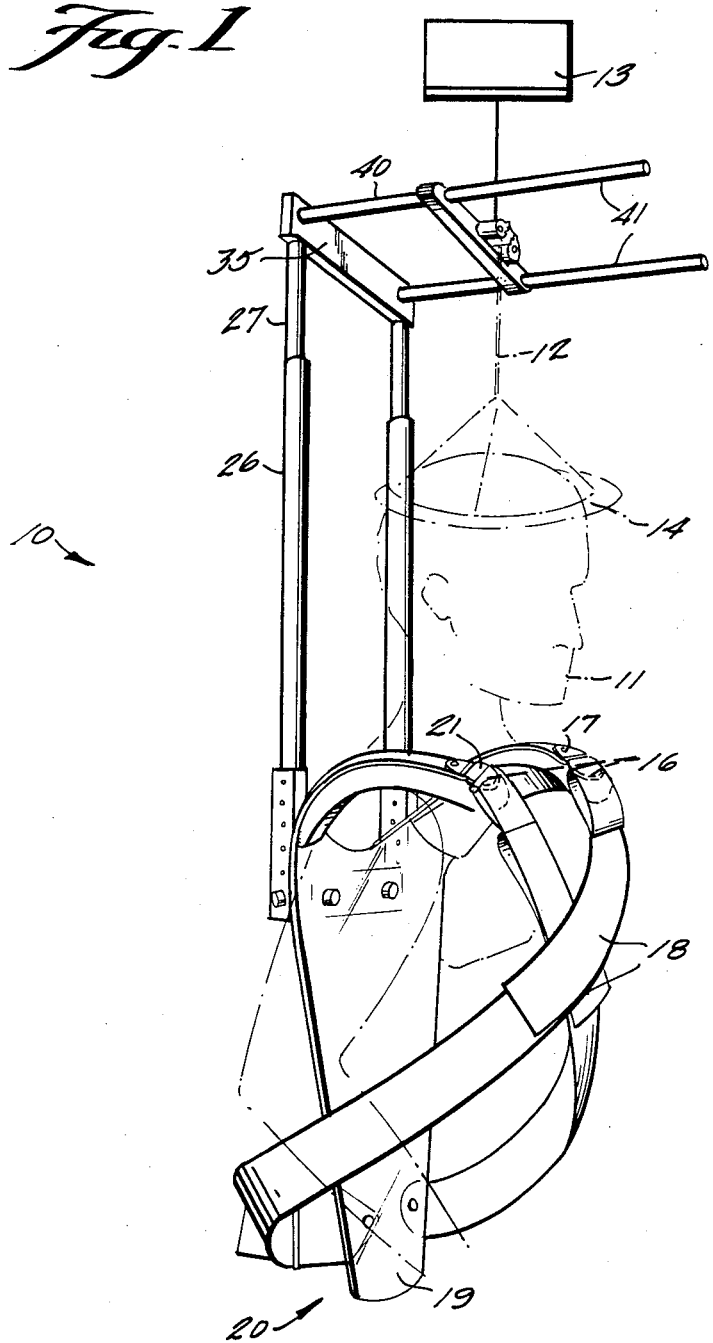
FIG. 1 is a perspective view illustrating an exemplary portable cervical traction device according to the invention shown in operative association with a patient, the patient being shown in dotted line.

The device according to the present invention is shown generally by reference numeral 10 in FIG. 1 and is adapted to be utilized with a patient 11 who is being maintained in cervical traction at a permanent traction station. Typical traction devices include a component for attaching the patient's head to a traction cable 12 (the term "cable" being generic to straps, ropes, strands, etc.), the cable 12 being attached to a suitable conventional traction applying mechanism 13, such as weights. Typical mechanisms for attaching the cable 12 to a patient's head include a cervical strap, tongs, and halo. A device 10 according to the present invention is versatile enough to be utilized with all such devices. In FIG. 1 the device 10 is shown in operative association with a patient 11 having a halo 14 attached to his head.

The device 10 according to the invention includes a pair of shoulder supports 16 which are adapted to engage the patient's shoulders. The shoulder supports 16 include relatively rigid components which are padded on the inside thereof, the padding adapted to engage the patient's shoulders, and have structures 17 formed thereon for attachment to the ends of a pair of chest straps 18.

The shoulder supports are preferably attached to a backplate 19 of radiolucent material. Preferably, the backplate 19 and the rigid portions of the shoulder supports 16 are formed from an integral piece of Lexan, or like material. The chest straps 18 operatively engage the backplate 19 at the bottom 20 thereof, with the free end of each of the chest straps 18 having a buckle 21, or the like, associated therewith to be attached to the structures 17 on the shoulder supports 16.

The components 16 through 21 are adapted to support the device 10 on the patient. The other components of the device 10 are utilized for applying the necessary traction force to the patient to maintain the patient in cervical traction while he/she is being transported from one station to another.

Attached to the plate 19 is a lower cross bar 23 (FIG. 4), which may be attached to the plate 19 by bolts (not shown) passing through openings 24 formed in lower cross bar 23, and corresponding openings formed in the plate 19. Attached to the lower cross bar 23 and extending upwardly therefrom are two sets of telescoping components 25. Each set of components 25, as seen most clearly in FIGS. 3 and 4, comprises a tube 26, a rod 27 slideable in the tube 26, and a coil spring, or like compression spring, 28 disposed in the tube 26 and engaged by the bottom tip 29 of the rod 27. The tube 26 preferably includes a barrel clevis 30 at the bottom thereof, including a cylindrical projection 31 which extends upwardly into the tube 26 in an interference or press-fit therewith, and provides a surface engaging the spring 28. The bottom of the barrel clevis 30 has a plurality of openings 32 extending therethrough for receipt of bolts 33 for attaching the clevis 30 to the lower cross bar 23. The height of the components 25 above the cross bar 23 is adjusted depending upon the openings 32 through which the bolts 33 are passed.

The lower cross bar 23, and the barrel clevis 30, and any other components that are likely to be in alignment with a patient's body, preferably are formed of aluminum or a like radiolucent material.

Figure 4:
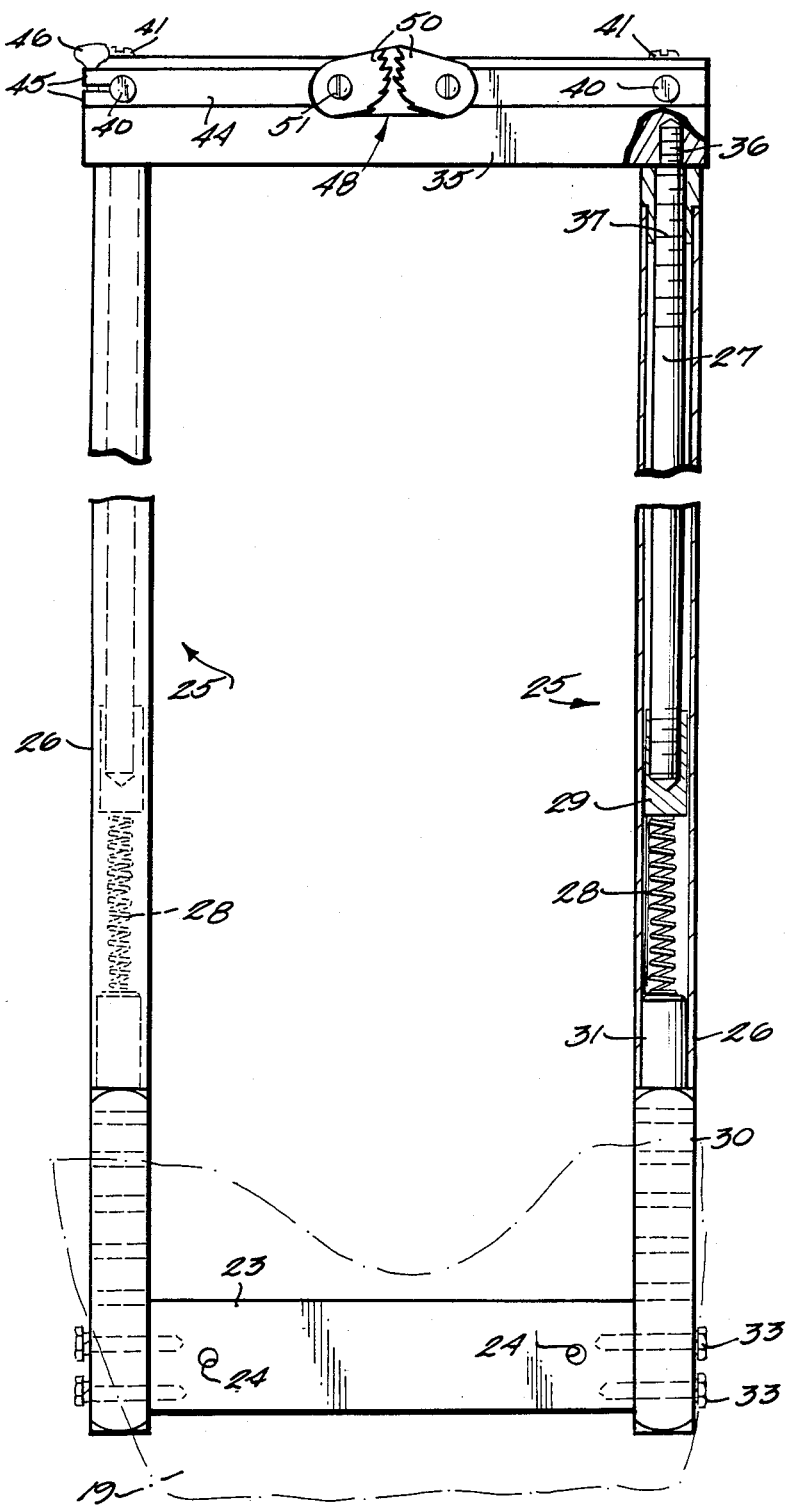
FIG. 4 is a front view, partly in cross-section and partly in elevation, of the device of FIG. 1.

Attached to the upper portions of the telescoping components 25 is the upper cross bar 35. The top ends of the rods 27 are preferably attached to the cross bar 35 by screwing the threaded ends 36 (see FIG. 4) thereof into threaded openings in the bottom of the cross bar 35. In FIGS. 3 and 4 the device is shown in a position of maximum compression of the springs 28 wherein the rods 27 have slid completely into the tubes 26.

As seen in FIG. 4, preferably scale markings 37 are provided on the portions of the rod 27 which may be exterior of the tube 26, the scale markings being related to the amount of biasing force being applied by the springs 28. When a particular scale marking 37 is in alignment with the top of the tube 26 the force being applied by the springs 28 is equal to the indicia provided associated with that scale marking (e.g. 10 pounds).

Releasably attached to the upper cross bar 35 are a pair slide rods 40. The slide rods 40 preferably are received in openings formed in the cross bar 35, and are held in place in the openings by clamping screws 41 or the like. When the clamping screws 41 are loosened, the rods 40 may be removed. The rods 40 extend generally perpendicular to a plane containing the cross bars 23, 35 and the components 25, and the slides rods 40 generally overhang the shoulder supports 16, as seen in FIG. 1. Each of the slide rods 40 has a free end 42 thereof distal from the cross bar 35.

Slideably mounted on the slide rods 40 is a slide bar 44. The slide bar 44 has an opening at one end (the right end in FIG. 4) thereof receiving one of the rods 40, and at the other end (the left end in FIG. 4) the slide bar 44 has a yoke construction, including a pair of yoke arms 45. The yoke arms 45 straddle a slide rod 40, and receive a thumb screw 46 in threaded openings formed therein. When the thumb screw 46 is tightened down the arms 45 are moved closer together, clamping the slide bar 44 in contact with a slide rod 40 and preventing sliding movement of the bar 44 with respect to the rods 40. When the thumb screw 46 is loosened, slideable movement between the slide bar 44 and rods 40 is possible.

The slide bar 44 has grasping means associated therewith for quickly releasably positively grasping the traction cable 12. It is important that the grasping means be able to quickly grasp, and readily release, the cable 12 in order to facilitate attachment of the device 10 to the patient. However it is also necessary that the grasping means positively hold the cable 12 in place in a desired position in order that cervical traction is properly maintained.

The grasping means preferably comprise a cam cleat 48, and a deck cleat 49. The cam cleat 48 is attached to one side of the slide bar 44, and the cleat components 50 are thus each mounted for pivotal movement about a horizontal axis (defined by the screws 51) parallel to the slide rods 40. The cam cleat 48 comprises a conventional clamp cleat such as used in sailboats.

Attached to the opposite side of the slide bar 44 as the cam cleat 48 (see FIG. 2) is the deck cleat 49. The deck cleat 49 may be attached, as by screws 52, in a rigid position with respect to the slide bar 44, and is positioned so that the tension cable 12 received by the cam cleat 48 may be wrapped therearound.

METHOD

In the utilization of the device 10 according to the present invention, the device 10 is first transported to the bed side of the patient 11 being maintained in cervical traction by cable 12 and structure 13, the bed comprising the stationary traction station. The patient 11 is log-rolled onto his/her side from a normal position, and the device 10 is placed on the patient's back. The straps 18 are positioned so that they extend outwardly from the backplate 19, and the slide bar 44 is in a position adjacent the upper cross bar 35. The device 10 may be readily positioned since the area between the slide rods 40 is clear, and the cable 12 may pass between the distal ends 42 of the slide rods 40 into that area.

The patient is then log-rolled back to his/her normal position, so that the patient's back engages the plate 19. The device 10 is then adjusted so that the shoulder supports 16 properly engage the patient's shoulders, and then the straps 18 are moved in a crossing fashion over the patient's chest, with the buckles 21 thereof attached to the structures 17 formed on the shoulder supports 16.

With the device 10 snuggly attached to the patient, the thumb screw 46 is loosened so that the slide bar 44 may be slid along the slide rods 40 away from the cross bar 35 until the cam cleat 48 comes into operative association with the traction cable 12. Once this occurs the thumb screw 46 is tightened down to hold the slide bar 44 in position with respect to the slide rods 40, and a force is supplied to the upper cross bar 35 moving it toward the lower cross bar 23.

The cross bar 35 is moved toward the cross bar 23 until the desired compression of the springs 28 has been effected. The biasing force applied by the springs 28 is determined by reading the scale markings 37 on one or both of the telescoping rods 27. The cross bar 35 will be maintained in the position to which is has been moved since the cam cleat 48 allows relative movement between it and the cable 12 in the downward direction, but clamps the cable 12 tightly in place and will not allow the cross bar 35 to move upwardly under the influence of the springs 28.

Once the appropriate spring force has been applied and the cable 12 is held by the cam cleat 48, the cable 12 may be detached from the traction applying mechanism 13 at the traction station. Once the cable 12 is detached from the device 13 the portions of the cable 12 above the cam cleat 48 are wrapped tightly around the deck cleat 49 to insure that the cam cleat 48 will not inadvertently release the cable 12.

Once the device 10 has been properly attached, the patient may be moved to any other suitable station. For instance if the patient is moved to a station wherein diagnostic or therapeutic radiation is to be applied, the patient may be placed in operative association with the radiation applying equipment while the device 10 is still in place. The radiolucent nature of the plate 19, and other components, insures that the device 10 will not interfere with the radiation procedure.

Once the patient has been moved to the other station, the patient may be readily transported back to the traction station. Once back at the traction station, the above-recited steps for applying the device 10 are reversed. That is, the cable 12 is removed from the deck cleat 49 and reattached to the traction apparatus 13; the cam cleat 48 is released, and the upper cross bar 35 is allowed to slide freely, but slowly, upwardly with respect to the lower cross bar 23 under the influence of springs 28; the slide bar 44 is moved back toward the cross bar 35; the straps 18 are detached and the shoulder supports 16 moved out of contact with the patient's shoulders; the patient is log-rolled off the plate 19; the device 10 is removed; and the patient is log-rolled back to his/her normal position.

It will thus be seen that according to the present invention a simple yet effective device and method have been provided for temporarily maintaining cervical traction on a patient while the patient is being transported from and back-to a permanent traction station. While the invention has been herein shown and described in what is presently conceived to be the most practical and preferred embodiment thereof, it will be apparent to those of ordinary skill in the art that many modifications may be made thereof within the scope of the invention, which scope is to be accorded the broadest interpretation of the appended claims so as to encompass all equivalent methods and devices.

What is claimed is:

1. A mobile cervical traction device for a patient, comprising:
    patient body-engaging support structures;
    a pair of upstanding support members operatively extending upwardly from said patient body-engaging support structures;
    a first cross bar operatively attached to, and extending between, the tops of the support members;
    a pair of slide rods operatively attached to said cross bar and extending outwardly therefrom generally perpendicular to a plane containing said cross bar and support members, and generally overlying said body-engaging support structures, the area between said slide rods being open between said cross bar and free distal ends of the said rods;
    a slide bar mounted to said slide rods for sliding movement with respect thereto; and
    cable grasping means mounted to said slide bar for quickly and releasably positively securing a traction cable to said slide bar.

2. A device as recited in claim 1 wherein said support members each comprise a pair of telescoping components with spring means therebetween for applying a force to said telescoping components biasing said cross bar away from said body-engaging support structures.

3. A device as recited in claim 2 wherein each of said support members consists of: a tube; a compression spring mounted in said tube; and a rod freely slideable in said tube and having an end thereof abutting said compression spring for effecting compression thereof when said rod is slid inwardly into said tube.

4. A device as recited in claim 2 wherein said cable grasping means comprises a cam cleat having a pair of relatively pivotal components pivotal about axes generally parallel to said slide rods.

5. A device as recited in claim 4 wherein said cam cleat, is mounted on one side of said slide bar, and wherein said cable grasping means further comprises a deck cleat mounted on the opposite side of said slide bar as said cam cleat.

6. An assembly as recited in claim 5 wherein said body-engaging support structures comprise shoulder-engaging support structures that are operatively attached to said upstanding support members by: a second cross bar; means for releasably attaching said shoulder support structures to said second cross bar; and means for adjusting the position of said lower cross bar with respect to said support members to securely hold said shoulder support members in different vertical positions with respect to said first cross bar.

7. A device as recited in claim 6 wherein said means for attaching said shoulder support structures to said lower cross bar comprises a plate of radiolucent material integral with said shoulder support structures; and wherein said means for attaching said shoulder support structures and said support members to a patient comprise a pair of straps operatively attached to said plate.

8. A device as recited in claim 1 wherein said cable grasping means comprises a cam cleat having a pair of relatively pivotal components pivotal about axes generally parallel to said slide rods.

9. A device as recited in claim 8 wherein said cam cleat is mounted on one side of said slide bar, and wherein said cable grasping means further comprises a deck cleat mounted on the opposite side of said slide bar from said cam cleat.

10. A device as recited in claim 8 further comprising means for readily releasably positively attaching said slide rods to said cross bar.

11. A device as recited in claim 1 further comprising means for readily releasably positively attaching said slide rods to said cross bar.

12. A method of temporarily maintaining cervical traction on a patient during movement of the patient from a stationary cervical traction position, including a traction cable and traction device, to another position, utilizing a portable cervical traction device including shoulder supports, a structure upstanding from the shoulder supports, a traction cable grasping structure releasably attached to said upstanding support, and means for releasably attaching the shoulder supports to the patient's body with the shoulder supports in contact with the patient's shoulders, comprising the steps of:
    (a) while the patient is maintained in traction at the stationary traction station, placing the shoulder supports, with upstanding structure, into operative contact with the patient's shoulders, and attaching the shoulder supports to the patient's body with the attachment means;
    (b) moving the traction cable grasping structure into operative association with the traction cable at the stationary traction station;

(c) applying suitable traction force to the shoulder supports and grasping the traction cable at a position thereof maintaining the force applied;

(d) releasing the traction cable from attachment to the traction device at the stationary traction station; and (e) transporting the patient, with portable cervical traction device applied, from the traction station to another station.

13. A method as recited in claim 12 wherein the major portions of the portable cervical traction device engaging the patient's body are of radiolucent material; and wherein step (e) is practiced by transporting the patient to a radiation station, and applying appropriate amounts of diagnostic or therapeutic radiation to the patient while the patient is maintained in cervical traction by the portable cervical traction device.

14. A method as recited in claim 12 comprising the further steps of: after transporting the patient to another station, returning the patient to the stationary traction station; reattaching the traction cable to the traction device at the stationary traction station; operatively disconnecting the cable grasping structure from the cable; and detaching the shoulder supports of the portable traction device from the patient.

15. A method as recited in claim 12 wherein the portable traction device includes a backplate, and comprises chest straps as the attachment means for attaching the backplate and shoulder supports to the patient; and wherein step (a) is practiced by: log-rolling the patient from a normal position to his/her side; placing the portable traction device at the normal position so that the backplate will engage the patient's back when he/she is rolled back to the normal position; log-rolling the patient back to the normal position; and placing the shoulder supports into contact with the patient's shoulders and attaching the chest straps over the patient's chest.

16. A method as recited in claim 15 wherein the cable grasping device comprising a cam cleat and a deck cleat; and wherein step (b) is practiced by moving the cam cleat into operative association with the traction cable; and wherein after the release of the traction cable from the stationary traction station in step (d), wrapping the traction cable around the deck cleat while the cable is held by the cam cleat.

17. A method as recited in claim 16 wherein the upstanding structure of the portable traction device comprises two sets of telescoping components with compression springs disposed between the telescoping components of each pair, the telescoping components being freely slideable with respect to each other; and wherein step (c) is practiced by sliding the telescoping components of each set with respect to each other to compress the springs associated therewith.

18. A method as recited in claim 17 wherein the telescoping components have scale markings thereon, and wherein step (c) is practiced by moving the telescoping components with respect to each other to compress springs associated therewith until the desired traction force is achieved as determined by viewing the scale markings on the telescoping components.

19. A portable cervical traction device comprising:
a pair of shoulder support structures;
a plate of radiolucent material operatively attached to said shoulder support structures and adapted to engage a patient's back;
strap means operatively attached to said plate for strapping said plate onto a patient's body with said shoulder support structures in contact with the patient's shoulders;
a traction support member operatively attached to said plate and extending upwardly therefrom, said traction support member comprising: a lower cross bar; an upper cross bar; means for attaching said lower cross bar to said plate; and two sets of telescoping components operatively attached to said upper and lower cross bars, with biasing means associated with said telescoping components of each set for providing a biasing force tending to separate said lower and upper cross bars, but allowing said lower and upper cross bars to be moved toward each other against said biasing force, with said biasing force gradually increasing as said upper and lower cross bars are moved toward each other; and
traction cable grasping means operatively attached to said upper cross bar.

20. A device as recited in claim 19 wherein said traction cable grasping means comprises a pair of slide rods extending generally perpendicular to a plane containing said upper and lower cross bars and telescoping components, and generally overhanging said shoulder supports, each of said slide rods having a free end thereof distal from said upper cross bar; a slide bar slideably movable on said slide rods; and cleat means for grasping and holding a traction cable, said cleat means attached to said slide bar and movable therewith over said slide rods.

* * * * *